(12) United States Patent
Fährenmark et al.

(10) Patent No.: US 7,993,899 B2
(45) Date of Patent: Aug. 9, 2011

(54) METHOD FOR THE PURIFICATION OF CHYMOSIN

(75) Inventors: Johan Fährenmark, Sollentuna (SE); Inger Lagerlund, Bromma (SE); Robert Morenweiser, Regensburg (DE); Mylene Caussette, Lille (FR); Eric Piron, Lambersart (FR)

(73) Assignees: GE Healthcare Bio-Sciences AB, Uppsala (SE); DSM IP Assets BV, Te Heerlen (NL)

( * ) Notice: Subject to any disclaimer, the term of this patent is extended or adjusted under 35 U.S.C. 154(b) by 1821 days.

(21) Appl. No.: 10/451,449

(22) PCT Filed: Dec. 19, 2001

(86) PCT No.: PCT/EP01/15047
§ 371 (c)(1),
(2), (4) Date: Dec. 1, 2003

(87) PCT Pub. No.: WO02/50253
PCT Pub. Date: Jun. 27, 2002

(65) Prior Publication Data
US 2004/0072320 A1    Apr. 15, 2004

(30) Foreign Application Priority Data
Dec. 20, 2000  (SE) ....................... 0004808

(51) Int. Cl.
*C12N 9/48* (2006.01)
*C07K 1/16* (2006.01)

(52) U.S. Cl. ............... 435/212; 435/195; 424/94.63; 424/94.64

(58) Field of Classification Search ............ 435/226, 435/183, 195, 212; 530/344; 424/94.63, 424/94.64
See application file for complete search history.

(56) References Cited

U.S. PATENT DOCUMENTS

| | | | |
|---|---|---|---|
| 4,666,843 A | 5/1987 | Subramanian | 435/226 |
| 4,721,673 A | 1/1988 | Uren et al. | 435/183 |
| 4,743,551 A | 5/1988 | Subramanian | 435/226 |
| 4,745,063 A | 5/1988 | Birschbach | 435/226 |
| 5,652,348 A | 7/1997 | Burton et al. | |
| 5,789,578 A * | 8/1998 | Burton et al. | 536/56 |
| 5,888,966 A | 3/1999 | Larsen et al. | 514/2 |
| 5,945,520 A | 8/1999 | Burton et al. | 536/20 |
| 6,057,131 A * | 5/2000 | Marsh et al. | 435/69.1 |
| 6,143,853 A * | 11/2000 | Ericsson et al. | 526/332 |
| 2001/0039043 A1 * | 11/2001 | Lihme et al. | 435/212 |
| 2002/0164696 A1 * | 11/2002 | Kappeler et al. | 435/69.1 |
| 2005/0153418 A1 | 7/2005 | Van Beckhoven et al. | |

FOREIGN PATENT DOCUMENTS

| | | |
|---|---|---|
| DE | 280333 | 7/1990 |
| DE | 4323913 | 1/1995 |
| WO | WO 9600735 | 1/1996 |
| WO | WO 9609116 | 3/1996 |
| WO | WO 01/58924 A2 | 8/2001 |
| WO | WO 03/100048 A1 | 12/2003 |

OTHER PUBLICATIONS

Sigma Catalog (1998) p. 1903.*
Burton et al. "High-density ligand attachment to brominated allyl matrices and application to mixed mode chromatography of chymosin" J. Chromatography (1997) 775: 39-50.*
Grznarova et al. "Quantitative characteriazation of pore structure of cellulose gels with or without bound protein ligand" Journal Chromat. A (2005) 1092: 107-113.*
Peters et al. "Rigid macroporous polymer monoliths" Adv. Materials (1999; published on-line Oct. 6, 1999) 11(14): 1169-1181.*
Perloza MT Product Information Sheet: www.perloza.cz/en/dmte.htm downloaded on Jul. 30, 2009.*
Grant & Hackh's Chemical Dictionary. (1987) 5th edition. Grant and Grant, eds. (McGraw-Hill Company: New York), p. 24.*
Burton et al. (1997). "One-step purification of chymosin by mixed mode chromatography" *Biotech. Bioengin.* 56(1):45-55.
US 5,122,467, 06/1992, Heinsohn et al (withdrawn)

* cited by examiner

*Primary Examiner* — Sandra Saucier
*Assistant Examiner* — Susan Hanley
(74) *Attorney, Agent, or Firm* — Nixon & Vanderhye, PC

(57) ABSTRACT

We describe a method for purifying chymosin comprising providing an aqueous liquid sample containing chymosin and a separation medium comprising a base matrix and a plurality of firmly attached ligands that are capable of binding to chymosin, contacting the matrix with the sample under conditions permitting binding of chymosin to the matrix, and desorbing chymosin from the matrix. The characterizing feature is that the matrix is hydrophilic and that the ligands in the plurality of ligands are hydrocarbon groups in which all carbon atoms are $sp^3$-hybridised, possibly with an ether oxygen or a thioether sulphur inserted between two carbon atoms at one or more positions in at least one of the hydrocarbon groups, and possibly a hydroxy group replacing a hydrogen atom at one or more positions in at least one of the hydrocarbon groups.

40 Claims, No Drawings

METHOD FOR THE PURIFICATION OF CHYMOSIN

CROSS-REFERENCE TO RELATED APPLICATION

This application is the national phase of PCT application PCT/EP01/15047 having an international filing date of 19 Dec. 2001, and claims priority from European application SE 0004808-2 filed 20 Dec. 2000. The contents of these documents are incorporated herein by reference.

TECHNICAL FIELD

The present invention relates to a method for purifying chymosin comprising the steps of:
(i) providing an aqueous liquid sample containing chymosin and a separation medium comprising a hydrophilic base matrix and a plurality of firmly attached ligands that are capable of binding to chymosin,
(ii) contacting the matrix with the sample under conditions permitting binding of chymosin to the matrix, and
(iii) desorbing chymosin from the matrix.

By the term chymosin is meant the aspartic protease zymogen and any intermediate form derived thereof which is proteolytically active or inactive. Included are also the various types of chymosin naturally occurring (type a, b c) as well as derived by genetic engineering and recombinant techniques.

TECHNICAL BACKGROUND

Chymosin is a milk-clotting enzyme that derives from the stomach of mammals where it is produced together with other milk-clotting enzymes, such as pepsin. Preparations of milk-clotting enzymes are used in food industry, for instance cheese manufacture. Thus there is a need for purified chymosin preparations having a high and well characterized specific milk-clotting activity.

Originally chymosin was purified from extracts of bovine stomach, in particular of calves. One main problem with this kind of natural sources have been that the extracts will contain also other milk-clotting enzymes, such as pepsin, and also various proforms of the enzymes. Accordingly earlier purification protocols included steps for transforming proforms to active enzymes and steps separating chymosin from pepsin. Another main problem has been that the activity of the starting material has varied significantly.

Separations of chymosin from pepsin has primarily utilized ion exchange adsorption combined with the fact that there is a large difference in isoelectric points for pepsin and chymosin (pI 2 and pI 4.8, respectively). In other words a cation exchanger which can be negatively charged in the interval pH 2-4.8 will be able to adsorb chymosin in this pH range. In the analogous fashion an anion exchanger which can be positively charged in the same pH interval will be capable of adsorbing chymosin. This has been utilized for instance in U.S. Pat. No. 5,888,966 (Larsen et al) and U.S. Pat. No. 4,745,063 (Birschbach). Affinity adsorption based on dye affinity ligands has also been suggested in U.S. Pat. No. 4,666,843 (Subramanian et al)

Chymosin has also been obtained by so called recombinant techniques, i.e. from host cells that have been transformed to produce chymosin (or proforms thereof). In this case other purification problems arise because the contaminants are not the same, for instance pepsin is lacking (unless the host cell also produce pepsin) and other contaminants have to be removed. Typical host cells can be of microbial origin, such as yeast, fungi (in particular *Asperigillus niger*), bacteria etc without exclusion of mammalian cells. For this kind of chymosin U.S. Pat. No. 4,743,551 (Subramanian) and U.S. Pat. No. 4,721,673 (Subramanian et al) propose dye affinity ligand adsorption and U.S. Pat. No. 5,122,467 (Heinsohn et al) proposes adsorption to phenyl SEPHAROSE® matrix (SEPHAROSE® is the trade mark of Amersham Pharmacia Biotech. The corresponding products are based on agarose). U.S. Pat. No. 5,122,467 (column 3, lines 31-50) suggests that a comparison has been made between phenyl SEPHAROSE® matrix and agaroses having other functionalities, including octyl. The conclusion stated is that the phenyl functionality is the only one providing the required selectivity for chymosin in fermentation broths. Experiments have also been presented to use other ligands containing aromatic rings in WO 9600735 (Burton et al) and WO 9609116 (Burton et al).

In recent study be Burton et al ("One-step purification of chymosin by mixed mode chromatography" in Biotech. Bioengin. 56(1) (1997) 45-55) a number of chargeable and non-chargeable aromatic ligands have been examined for adsorption of chymosin from a fermentation broth.

In spite of the number of previously suggested purification protocols there is still a need for improvements relating to yield/recovery, purity, specific chymosin activity, simplicity of operation, need for elution agents etc.

OBJECTIVES OF THE INVENTION

The first objective is to provide adsorption/desorption protocols for chymosin, which results in improvements relating to at least one of yield/recovery, purity, specific chymosin activity, simplicity of operation, need for elution agents etc.

The second objective is a method for optimising at least one of yield/recovery, purity, specific chymosin activity, simplicity of operation, need for elution agents etc.

An improvement may relate to the adsorption/desorption step as such or to the overall process. In other words an increase in purity in the adsorption/desorption step can imply that a preceding step normally carried out may be unnecessary.

THE INVENTION

The present inventors have recognized that these objectives can be at least partially complied with if the ligands are non-aromatic hydrocarbon groups. This is contrary to what has been suggested in U.S. Pat. No. 5,122,467 (Heinsohn et al).

The first aspect of the invention thus is a method as defined under the heading "Technical Field". The characterising feature of the method teaches that the matrix is hydrophilic and that the ligands in the plurality of ligands are hydrocarbon groups in which all the carbon atoms are $sp^3$-hybridised.

The hydrocarbon groups may or may not be identical.
The Ligand

The hydrocarbon groups may be straight, branched or cyclic. They may contain 1-30 carbon atoms, typically 3-25 carbon atoms.

In the hydrocarbon groups an ether oxygen atom (—O—) or a thioether sulphur atom (—S—) may have been inserted between two carbon atoms at one or more positions in at least one of the hydrocarbon groups that is present in the separation medium used. A hydrogen atom that binds to a carbon atom may have been replaced with an hydroxy group at one or more positions. The ratio of the sum of sulphur atoms and oxygen atoms to the number of carbon atoms in each hydrocarbon group is typically<1, with preference for $\leq 0.8$ or $\leq 0.5$ or $\leq 0.25$.

General stability requirements apply to the hydrocarbon groups meaning that both an ether oxygen atom and a thioether sulphur atom require binding to $sp^3$-hybridised carbon atoms in both directions. Further each $sp^3$-hybridised carbon atom in a hydrocarbon group should bind to at most one heteroatom selected amongst ether oxygen atoms, hydroxy oxygen atoms and thioether sulphur atoms.

The hydrocarbon group may contain one or more pure alkyl groups which also includes pure alkylene groups, i.e. hydrocarbon groups in which there are only hydrogen atoms and $sp^3$-hybridised carbon atoms. Typical pure alkyl/alkylene groups have 1-12 carbon atoms with preference for 2-10, such as 3-10, carbon atoms. These alkyl groups may be straight, branched or cyclic.

Typical hydrocarbon groups that may be ligands are:

Pure alkyl groups as discussed above. Illustrative examples are methyl, ethyl, n-propyl, isopropyl, n-butyl, sec-butyl, tert-butyl, various isoforms of pentyl, hexyl, heptyl, octyl etc. For pentyl and higher homologues the groups may contain cyclic structures.

Hydrocarbon groups that are obtainable by hydroxy alkylation of a base matrix, e.g. 2-hydroxy alkyl groups.

Hydrocarbon groups that are obtainable by reacting a base matrix with dialkyl ethers in which one or both of the alkyl groups contains an epoxy group, for instance the use of glycidyl alkyl ether for insertion of the group —[$CH_2CH(OH)CH_2O$]$_m$R where R is a pure alkyl group containing a cyclic structure ($C_nH_{2n-1}$) or only a straight and/or branched structure ($C_nH_{2n+1}$) and m and n are integers $\geq 1$.

The ligands are preferably hydrocarbon groups comprising three, four or five carbon atoms, more preferably four carbon atoms.

In addition to ligands comprising the above-defined hydrocarbon groups there may also be other kinds of ligands in the separation medium.

Spacer

The ligands/hydrocarbon groups may or may not have been immobilized to the base matrix via a spacer. In the context of the invention, the spacer is considered to start at the base skeleton of the base matrix and ends immediately after (a) the last heteroatom that is not a thioether atom or an ether atom, or (b) the last sp- or $sp^2$-hybridised carbon atom, which is part of the chain linking the ligand to the base matrix. If every heteroatom is an ether oxygen atom or a thioether sulphur atom and every carbon atom is $sp^3$-hybridised, there is no spacer (the ligand is attached directly to the base matrix).

The spacer, if present, thus may comprise groups selected from ether groups, thioether groups, bivalent hydrocarbon groups, ester groups, amide groups, azo groups, sulphone groups etc as well known in the field. The only proviso is that the terminal of the spacer which is distal to the base matrix, can not be an ether atom or a thioether atom or an $sp^3$-hybridised carbon atom. A bivalent hydrocarbon group in a spacer has a chain of $sp^3$-hybridised carbons that may carry uncharged or unchargeable substituent groups and may contain straight, branched or cyclic structures. Amide groups may be N-substituted with alkyl, which possibly in turn is substituted with one or more hydroxy groups, as described for hydrocarbon groups above.

In one and the same separation medium the hydrocarbon ligands may or may not be linked to the base matrix via a spacer. There may also be present different spacers as defined above.

In the most typical case the length of the spacer is 1-20 atoms (the chain of atoms between the base skeleton of the base matrix and the ligand). A single heteroatom, such as an ether oxygen atom, which is derived from the base matrix and used to anchor the spacer or the ligand to the base matrix is part of the base matrix and not of the spacer or ligand.

Normal stability requirement applies to the spacer, for instance at most one heteroatom selected amongst sulphur, oxygen and nitrogen should bind to one and the same $sp^3$-hybridised carbon atom.

Base Matrix

The base matrix is based on organic and/or inorganic material.

The base matrix is preferably hydrophilic and in the form of a polymer, which is insoluble and more or less swellable in water. Hydrophobic polymers that have been derivatized to become hydrophilic are included in this definition. Suitable polymers are polyhydroxy polymers, e.g. based on polysaccharides, such as agarose, dextran, cellulose, starch, pullulan, etc. and completely synthetic polymers, such as polyacrylic amide, polymethacrylic amide, poly(hydroxyalkylvinyl ethers), poly(hydroxyalkylacrylates) and polymethacrylates (e.g. polyglycidylmethacrylate), polyvinylalcohols and polymers based on styrenes and divinylbenzenes, and copolymers in which two or more of the monomers corresponding to the above-mentioned polymers are included. Polymers, which are soluble in water, may be derivatized to become insoluble, e.g. by crosslinking and by coupling to an insoluble body via adsorption or covalent binding. Hydrophilic groups can be introduced on hydrophobic polymers (e.g. on copolymers of monovinyl and divinylbenzenes) by polymerization of monomers exhibiting groups which can be converted to OH, or by hydrophilization of the final polymer, e.g. by adsorption of suitable compounds, such as hydrophilic polymers.

Suitable inorganic materials to be used in base matrices are silica, zirconium oxide, graphite, tantalum oxide etc.

The matrix may be porous or non-porous. This means that the matrix may be fully or partially permeable (porous) or completely impermeable to the compound to be removed (non-porous). For preparative processes the pore sizes should be such that matrix has a Kav which is in the interval 0.10-0.95 for chymosin, where the subinterval 0.40-0.95 in particular applies to base matrices which are devoid of so-called extenders. See below.

In a particularly interesting embodiment of the present invention, the matrix is in the form of irregular or spherical particles with sizes in the range of 1-1000 μm, preferably 5-50 μm for high performance applications and 50-300 μm for preparative purposes.

An interesting form of matrices has densities higher or lower than the liquid. This kind of matrices is especially applicable in large-scale operations for fluidised or expanded bed chromatography as well as for different batch wise procedures, e.g. in stirred tanks. Fluidised and expanded bed procedures are described in WO 9218237 (Amersham Pharmacia Biotech AB) and WO 92/100799 (Kem-En-Tek).

The term "a hydrophilic base matrix" in practice means that the accessible surface of the base matrix is hydrophilic in the sense that it is penetrated by aqueous liquids. Typically the accessible surfaces on a hydrophilic base matrix expose a plurality of polar groups for instance comprising oxygen and/or nitrogen atoms. Examples of such polar groups are hydroxyl, amino, carboxy, ester, ether of lower alkyls (such as (—$CH_2CH_2O$—)$_n$H where n is an integer).

If present, extenders, tentacles and the like as described in WO 9833572 (Amersham Pharmacia Biotech AB) are considered to be part of the base matrix.

Binding Capacity for Chymosin

Contrary to the findings presented in U.S. Pat. No. 5,122,467 (Heinsohn et al), the present inventors have recognized that separation media based on hydrophilic base matrices and the proper hydrophilic/hydrophobic balance that may be caused by the presence of the above-mentioned hydrocarbon groups can be used in improved separation protocols for chymosin. The binding ability should be sufficient to give a sufficient binding capacity, and binding strength permitting desorption under conditions not causing irreversible denaturation of chymosin. The ligand n-butyl-OCH$_2$CHOHCH$_2$-linked to SEPHAROSE® FAST FLOW matrix as described in the experimental part will work well for the less hydrophobic variants B and C while the more hydrophobic variants A will give a lowered yield in the desorption step.

It follows from the preceding paragraph that the efficiency of different separation media will vary with the hydrophilic/hydrophobic balance in the base matrix, with substitution degree of the hydrocarbon groups (ligands) and with the hydrophilic/hydrophobic balance in the ligand (hydrocarbon group). Taking into account the large number of different base matrices available and the large number of different ligands it becomes impossible to give a range for the substitution degree unless a wide interval is set, such as 0-500, such as 0-100 or 5-500, μmol/ml wet gel. The extreme value 0 μmol/ml wet gel stands for the case where the base matrix as such provide the proper hydrophobic/hydrophilic balance.

In order to determine if a certain separation medium is efficient or optimal for chymosin purification, we have developed a method for determining the hydrophilic/hydrophobic balance of separation media. The method is described in the experimental part and means that a separation medium is packed in a column whereafter α-chymotrypsinogen is allowed to pass through under the standard conditions given. Suitable separation media to be used in the invention are found amongst those media that in this test give a retention time (r) for α-chymotrypsinogen which is within the interval $r_{standard} \pm 50\%$ where $r_{standard}$ is the retention time for α-chymotrypsinogen on variant B of n-butyl-OCH$_2$CH(OH)CH$_2$-SEPHAROSE® FAST FLOW matrix described in the experimental part. Optimal variants normally have retention times within the interval: $r_{standard} \pm 10\%$.

A second aspect of the invention is a method for purifying chymosin comprising the steps of:
(i) providing an aqueous liquid sample containing chymosin and a separation medium comprising a hydrophilic base matrix,
(ii) contacting the matrix with the sample under conditions permitting binding of chymosin to the matrix, and
(iii) desorbing chymosin from the matrix.

In this aspect of the invention the characterizing feature is that the separation medium has a hydrophilic/hydrophobic balance that in the test given in the experimental part gives a retention time (r) for α-chymotrypsinogen which is within the interval $r_{standard} \pm 50\%$ where $r_{standard}$ is the retention time for α-chymotrypsinogen of variant B of n-butyl-OCH$_2$CH(OH)CH$_2$-SEPHAROSE® FAST FLOW matrix described in the experimental part. Optimal variants normally are found amongst those separation media which have retention times within the interval: $r_{standard} \pm 10\%$.

The separation medium used in this aspect of the invention may or may not have ligands, spacers as defined for the first aspect of the invention. The base matrix is as defined above for the first aspect. If no ligands of the kind defined above are present the medium always lacks other ligands which comprise an aromatic ring structure.

The Protocol for Carrying out the Adsorption/Desorption

The adsorption step is typically carried out under conditions promoting adsorption, which means aqueous liquids with non-denaturing pH for chymosin and a relatively high ionic strength, for instance corresponding to a salt concentration within the interval 0.1-2 M Na$_2$SO$_4$. (in particularly corresponding to >0.2 M Na$_2$SO$_4$). The pH is preferably below or around the pi (i.e. 4.8) of chymosin, i.e. in the interval of pH of between 2 and 5, preferably between 3.5 and 4.8 and more preferably between 4.0 and 4.5. This ionic strength may have been accomplished by adding water soluble salts for instance salts of the Group IA and II B elements such as chlorides, sulphates etc including also corresponding ammonium salts. Particularly valuable salts in this respect are NaCl, NH$_4$Cl, Na$_2$SO$_4$ and (NH$_4$)$_2$SO$_4$.

After the adsorption step the separation media can be washed with an aqueous media of appropriate ionic strength and pH. Illustrative ionic strengths corresponds to the interval 0.1-2.0 M Na$_2$SO$_4$ (in particularly corresponding to >0.2 M Na$_2$SO$_4$, and the pH in the interval 3.5-7.5. The salts present in the washing solutions are selected amongst the same kind as used for the adsorption step.

Finally chymosin is desorbed from the separation medium by decreasing the ionic strength/salt concentration until desorption occurs. The exact ionic strength/salt concentration at which desorption will occur depends on the particular separation medium used. The salt concentration may often be selected in the interval 0.0-1M Na$_2$SO$_4$ or the corresponding ionic strength if other salts are used. As a rule of thumb the ionic strength for desorption typically is below the ionic strength of 1.0 M Na$_2$SO$_4$. In particular if the pH has been below the pI for chymosin during the adsorption the decrease in ionic strength can be combined with an increase in pH, for instance in the interval of pH between 5.0 and 8.0, preferably between 6.0 and 7.0 and more preferably between 6.4 and 6.8. The salts incorporated in the desorption solutions may be selected amongst the same salts as for the adsorption solution.

The change in ionic strength and/or pH during desorption can take place as a stepwise or continuous gradient. A stepwise gradient may contain one or more steps. The change in pH may take place after, before or simultaneously with the change in ionic strength. The initial experiments were performed at an constant pH 25 of 5.0. (loading and elution). The purity of the chymosin was similar but the yield about 10% lower and the volume of elution was higher.

Typical buffer substances are water-soluble acetates, citrates, phosphates, in particular sodium phosphates, etc and the proper choice depends on the desired 30 pH.

The preferred protocol is given in the experimental part.

The adsorption and/or desorption steps may be carried out as a batch process in which the separation medium is agitated for instance by stirring or by a through-flowing aqueous liquid. Most preferably, the inventive method is carried out as a chromatographic process, i.e. with the separation media in form of particles/beads that are packed to a bed or fluidised to an expanded bed. For chromatographic processes the separation medium can also be in monolithic form, for instance in form of a plug or a filter.

In preferred variants, the inventive process is cyclic, i.e. the separation medium is recovered after step (iii) and reused in step (i), possible with a regeneration step and/or cleaning step inserted between step (iii) and step (i) of a subsequent cycle. Regeneration/cleaning solutions typically contain NaOH (for instance >0.1 M, such as 0.5 or 1 M). By including isopropanol it is possible to reduce the NaOH concentration.

The yield of chymosin obtained in the desorption step is typically ≧60% such as ≧85% of the total amount of chymosin provided in the sample applied. One cannot exclude that the yield can be equal or exceed 90% in this step. The purity of purified chymosin is advantageously above 90% on protein (based on peak area determination at 280 mm in the chromatogram) as determined by analysis with the aid of high performance liquid chromatography based on size exclusion (HPLC-SEC, see further the experimental part). Preferably the purity is more than 92%, and more preferably more than 95%).

The inventive method may also comprise additional steps either before or after steps (i)-(iii) as described above. Preceding steps includes for instance transforming prochymosin, pseudochymosin etc to fully active chymosin, precipitation, filtration, other adsorption steps etc as is well known in the field of protein purification. Potential subsequent steps are desalting, polishing steps that typically means further purification for instance by affinity adsorption, drying for instance by lyophilization or spray-drying, etc.

The inventive method is in particular adapted to recombinant forms of chymosin from preparations that are essentially free of pepsin.

EXPERIMENTAL PART

Synthesis of Prototype Separation Media

Rinse 100 ml SEPHAROSE® 4 FAST FLOW matrix (Amersham Pharmacia Biotech, Uppsala, Sweden) on a glass filter funnel with at least 10 gel volumes of distilled water. Transfer the base matrix to the reaction tank. Adjust the total volume, see table 1, with distilled water and start agitation. Add 16.5 g sodium sulphate, sodium hydroxide 50%, see table 1, and 0.2 g sodium borohydride. Allow the salts to dissolve under at least 1 h. Raise the temperature to 50° C. and add butyl glycidyl ether, see table 1. Let the reaction run at 50±3° C. for 17-24 hours. Reduce the temperature to 20-25° C. Add acetic acid to get a pH of 5-7. Rinse the adsorbent on a glass filter funnel with at least 2 gel volumes of distilled water, 6 gel volumes of ethanol and finally with 10 gel volumes of distilled water. Store the media in 20% ethanol.

TABLE 1

| Prototype | Total volume (ml) | Sodium hydroxide 50% (g) | Butyl glycidyl ether (g) |
|---|---|---|---|
| A | 120 | 34 | 23.0 |
| B | 133 | 29 | 16.7 |
| C | 125 | 32 | 18.0 |

Testing for Hydrophobic/hydrophilic Balance
Adsorption Buffer
0.02 M Tris-(hydroxymethyl)-aminomethane+1.70 M ammonium sulphate, adjusted to pH 7.5±0.1 with hydrochloric acid.
Elution Buffer
0.02 M Tris-(hydroxymethyl)-aminomethan to pH 7.5±0.1 with hydrochloric acid.
Sample

| α-chymotrypsinogen | 1.0 mg/ml |
|---|---|

The protein is dissolved in adsorption buffer
Column Packing
Wash approximately 25 ml gel on a glass filter funnel with 250 ml distilled water, and then with 100 ml desorption buffer in small portions. Pack 10 ml gel in each column with a flow rate of 2 ml/minute and adjust the bed height to 10.5-11.0 cm. Mount the top adaptor and pack for 20 minutes more with a flow rate of 4 ml/minute. Mark the bed height during flow, and adjust the top adaptor just below the bed surface. The bed height should now be 10±0.2 cm.
Chromatographic Procedure The test is performed at 23±0.5° C.
Equilibrate with 39 ml of adsorption buffer at a flow rate of 1 ml/minute.
Inject 1.0 ml of protein mixture with a flow rate of 0.5 ml/minute
Elute the proteins with a gradient, 0-100%, of desorption buffer at a flow rate of 1 ml/minute for 60 minutes.
The retention time is the time from the gradient starts until peek maximum of the proteins is eluted.
All three prototypes were tested according to protocols given above. The test results are given in table 2

TABLE 2

| Protoype | Retention time for α-chymotrypsinogen (min) |
|---|---|
| A | 68 |
| B | 58 |
| C | 62 |

By varying the components in the reaction mixture the same hydrophobic/hydrophilic balance could be obtained by different routes for a given combination of alkyl glycidyl ether and base matrix.

Commercially available Octyl SEPHAROSE® FAST FLOW matrix was tested in this method and found to have a retention time of 45±4 min. When tested in the chromatographic procedure given above for binding chymosin it was found that the binding was weaker. These results suggest that in order to have an octyl variant based on SEPHAROSE® FAST FLOW matrix with similar binding of chymosin as variants B and C above, a more hydrophobic variant has to be synthesized, for instance by varying the conditions under which the octyl group is introduced.
Chromatographic Experiments with Chymosin.

EXAMPLE 1

The example describes the chromatographic purification of chymosin using variant B above SEPHAROSE® 4 FAST FLOW matrix derivatized by reaction with butyl glycidyl ether.

The chymosin sample has been obtained from a fermentation process of a genetically modified Kluyveromyces host strain as described in the patent EP 301679 (Rietveld et al.)

About 20,000 IMCU of chymosin activity was loaded onto a column of 4.6×150 mm packed with separation medium variant B described above at a linear flow rate of 200 cm/h. The column was equilibrated with 25 mM NaAc, pH 4.0, 0.35 M $Na_2SO_4$. The chymosin capacity for the separation medium was 8000 iMCU wet medium (35 mg/ml wet resin).

After loading the column was washed with equilibration buffer (200 cm/h) until the baseline was reached. Elution of chymosin was done by a step gradient at 200 cm/h (50 mM potassium phosphate buffer, pH 6.5). Typically, chymosin was eluted as a single peak.

The eluted chymosin had a protein purity of 98% based on HPLC-SEC analysis. The process yield was about 85%. Chymosin concentration was determined according to International Dairy Federation 157, Remcat method.

The HPLC-SEC analysis was made on TSK G 3000 SW, TosoHaas-7.5 mm ID-30 mm, mobile phase 0.1 M $NaH_2PO_4$, pH 5.8, 1.0 ml/min.

EXAMPLE 2

The example describes the chromatographic purification of chymosin using variant B of SEPHAROSE® 4 FAST FLOW matrix derivatized by reaction with butyl glycidyl ether and 1,2 propandiol as an additive in the elution buffer.

A chymosin containing process fluid was loaded onto a column containing the separation medium as described in example 1. After loading the column was washed with equilibration buffer (200 cm/h) until the base line was reached. Elution of chymosin was done by a step-gradient at 200 cm/h using 50 mM potassium phosphate, pH 6.5 with 5% 1,2-propanediol. Chymosin eluted in one single peak. The elution volume was reduced by 22% compared to example 1.

EXAMPLE 3

This example describes a capacity study using variant B media of butyl SEPHAROSE® 4 FAST FLOW matrix for a chymosin sample that has been obtained from a fermentation process. Loading conditions were according to example 1. Flow through fraction were analysed for chymosin activity.

From a plot percentage of "load in the flow through" versus "load of chymosin (cleared process fluid)/ml separation medium" it was determined that the breakthrough capacity of this separation medium for chymosin was 8000IMCU ml/medium at 10% breakthrough in the flow through.

The specific activity of chymosin is 230 IMCU/g and therefore the binding capacity of this separation medium is 35 mg/ml. The binding capacity of 35 mg/ml is high compared with the prior art. U.S. Pat. No. 5,122,467 (phenyl SEPHAROSE® matrix) shows a binding capacity of 7 to 8 mg/ml.

EXAMPLE 4

Example 1 was repeated except that SEPHAROSE® 6 FAST FLOW matrix was used. By using SEPHAROSE 6® FAST FLOW matrix less compressibility was found during the chromatographic purification of chymosin. The binding capacity was found to be similar as described in Example 3. Finally we found that the superficial velocities could be applied now (up to 3 m/hour) at all stages of the purification process (loading, washing, elution), which is advantageous for pilot plant and industrial scale processes.

The invention claimed is:

1. A method for purifying chymosin comprising:
   (i) contacting an aqueous liquid sample containing chymosin with a separation medium comprising a base matrix and a plurality of attached ligands that are capable of binding to chymosin, wherein the pH of the aqueous sample is about or lower than the pI of chymosin and
   (ii) desorbing the chymosin with an aqueous buffer from the separation medium at a pH which is higher than the pI of chymosin, wherein said base matrix is hydrophilic and each ligand consists of
      a) a hydrocarbon group of 1-12 carbon atoms wherein all of the carbon atoms are $sp^3$-hybridized,
      b) a hydrocarbon group of 1-12 carbons atoms wherein all of the carbon atoms are $sp^3$-hybridized having one or more oxygen (O) or sulphur (S) atoms inserted between two carbon atoms of the hydrocarbon group, wherein the ratio of the sum of sulphur and oxygen atoms to the number of carbon atoms in each ligand is <1,
      c) a hydrocarbon group of 1-12 carbon atoms wherein all of the carbon atoms are $sp^3$-hybridized and at least one of the hydrogen atoms is substituted by a hydroxyl group, or combination of said ligands, wherein the separation matrix consists only of ligands of said hydrocarbon groups, wherein said base matrix is in the form of a porous monolith, and wherein the surfaces of the pores of said base matrix have sufficient hydrophilicity for the aqueous liquid sample to penetrate said pores.

2. The method of claim 1, wherein each of the ligands comprises a $C_{1-12}$ alkyl group.

3. The method of claim 2, wherein each of the ligands comprises a $C_{3-10}$ alkyl group.

4. The method of claim 1, wherein the ligands are directly attached to the base matrix by O or S said O or S being part of the base matrix.

5. The method of claim 1, wherein each ligand is attached to the base matrix via a spacer which has a bivalent functional group other than O or S which functional group is attached directly to ligands.

6. The method of claim 5, wherein the spacer comprises one or more structures selected from (a) straight, branched or cyclic bivalent hydrocarbon groups optionally substituted with hydroxy or lower alkoxy, (b) bivalent amide or (c) bivalent ester.

7. The method of claim 1, wherein the yield of chymosin is at least 80%.

8. The method of claim 1, wherein the purity of chymosin after step (ii) is at least 90% based on high performance liquid chromatography-size exclusion chromatography (HPLC-SEC) analysis.

9. The method of claim 1, wherein the chymosin to be purified is recombinantly produced.

10. The method of claim 1, wherein the chymosin to be purified has been obtained from the stomach of a mammal.

11. The method of claim 1, wherein the method is a chromatographic or batch-wise adsorption process.

12. The method of claim 1, wherein the base matrix is based on a polyhydroxy polymer.

13. The method of claim 12, wherein the base matrix is based on a cross-linked polyhydroxy polymer.

14. The method of claim 1, wherein the ratio of the sum of sulphur and oxygen atoms to the number of carbon atoms in each ligand is <0.25.

15. A method for purifying chymosin comprising:
   (i) contacting an aqueous liquid sample containing chymosin with a separation medium comprising a base matrix and a plurality of attached ligands that are capable of binding to chymosin, wherein the pH of the aqueous sample is about or lower than the pI of chymosin and
   (ii) desorbing the chymosin with an aqueous buffer from the separation medium at a pH which is higher than the pI of chymosin, wherein said base matrix is a cross-linked polyhydroxy polymer and the ligands consist of:
      a) a hydrocarbon group of 1-12 carbon atoms wherein all of the carbon atoms are $sp^3$-hybridized,
      b) a hydrocarbon soup of 1-12 carbons atoms wherein all of the carbon atoms are $sp^3$-hybridized having one or more oxygen (O) or sulphur (S) atoms inserted between two carbon atoms of the hydrocarbon group, wherein the ratio of the sum of sulphur and oxygen atoms to the number of carbon atoms in each ligand is <1, c) a hydrocarbon group of 1-12 carbon atoms wherein all of the carbon atoms are $sp^3$-hybridized and at least one of the hydrogen atoms is substituted by a hydroxyl group, or combination of said ligands, wherein the separation matrix consists only of ligands of said hydrocarbon groups, wherein said base matrix is in the form of a porous monolith, and wherein the surfaces of the pores of said base matrix have sufficient hydrophilicity for the aqueous liquid sample to penetrate said pores.

16. The method of claim 15, wherein each of the ligands comprises a $C_{1-12}$ alkyl group.

17. The method of claim 16, wherein each of the ligands comprises a $C_{3-10}$ alkyl group.

18. The method of claim 15, wherein the ligands are directly attached to the base matrix by O or S said O or S being part of the base matrix.

19. The method of claim 15, wherein each ligand is attached to the base matrix via a spacer which has a bivalent functional group other than O or S which functional group is attached directly to ligands.

20. The method of claim 19, wherein the spacer comprises one or more structures selected from (a) straight, branched or cyclic bivalent hydrocarbon groups optionally substituted with hydroxy or lower alkoxy, (b) bivalent amide or (c) bivalent ester.

21. The method of claim 15, wherein the yield of chymosin is at least 80%.

22. The method of claim 15, wherein the purity of chymosin after step (ii) is at least 90% based on HPLC-SEC analysis.

23. The method of claim 15, wherein the chymosin to be purified is recombinantly produced.

24. The method of claim 15, wherein the chymosin to be purified has been obtained from the stomach of a mammal.

25. The method of claim 15, wherein the method is a chromatographic or batch-wise adsorption process.

26. The method of claim 15, wherein the ratio of the sum of sulphur and oxygen atoms to the number of carbon atoms in each ligand is <0.25.

27. A method for purifying chymosin comprising:

(i) contacting an aqueous liquid sample containing chymosin with a separation medium comprising a base matrix and a plurality of attached ligands that are capable of binding to chymosin, wherein the pH of the aqueous sample is about or lower than the pI of chymosin and (ii) desorbing the chymosin with an aqueous buffer from the separation medium at a pH which is higher than the pI of chymosin, wherein said base matrix is hydrophilic and each ligand consists of a) a hydrocarbon group of 1-12 carbon atoms wherein all of the carbon atoms are $sp^3$-hybridized, b) a hydrocarbon group of 1-12 carbons atoms wherein all of the carbon atoms are $sp^3$-hybridized having one or more oxygen (O) or sulphur (S) atoms inserted between two carbon atoms of the hydrocarbon group, wherein the ratio of the sum of sulphur and oxygen atoms to the number of carbon atoms in each ligand is <1, c) a hydrocarbon group of 1-12 carbon atoms wherein all of the carbon atoms are $sp^3$-hybridized and at least one of the hydrogen atoms is substituted by a hydroxy group, or combination of said ligands, wherein the separation matrix consists only of ligands of said hydrocarbon groups, wherein said base matrix is in the form of porous beads or a porous monolith, and wherein the surfaces of the pores of said base matrix have sufficient hydrophilicity for the aqueous liquid sample to penetrate said pores, and wherein each ligand is attached to the base matrix via a spacer which has a bivalent functional group other than 0 or S which functional group is attached directly to ligands.

28. The method of claim 27, wherein each of the ligands comprises a $C_{1-12}$ alkyl group.

29. The method of claim 28, wherein each of the ligands comprises a $C_{3-10}$ alkyl group.

30. The method of claim 27, wherein the ligands are directly attached to the base matrix by O or S said O or S being part of the base matrix.

31. The method of claim 27, wherein the spacer comprises one or more structures selected from (a) straight, branched or cyclic bivalent hydrocarbon groups optionally substituted with hydroxy or lower alkoxy, (b) bivalent amide or (c) bivalent ester.

32. The method of claim 27, wherein the yield of chymosin is at least 80%.

33. The method of claim 27, wherein the purity of chymosin after step (ii) is at least 90% based on HPLC-SEC analysis.

34. The method of claim 27, wherein the chymosin to be purified is recombinantly produced.

35. The method of claim 27, wherein the chymosin to be purified has been obtained from the stomach of a mammal.

36. The method of claim 27, wherein the base matrix is in the form of beads in a packed or fluidised bed.

37. The method of claim 36, wherein the method is a chromatographic or batch-wise adsorption process.

38. The method of claim 27, wherein the ratio of the sum of sulphur and oxygen atoms to the number of carbon atoms in each ligand is <0.25.

39. The method of claim 27, wherein the base matrix is based on a polyhydroxy polymer.

40. The method of claim 39, wherein the base matrix is based on a cross-linked polyhydroxy polymer.

* * * * *